United States Patent [19]

Dalton

[11] Patent Number: 4,781,695
[45] Date of Patent: Nov. 1, 1988

[54] IMPLANTABLE FLUID DISPENSER

[76] Inventor: Michael J. Dalton, 9432 Monticello Ave., Evanston, Ill. 60203

[21] Appl. No.: 884,432

[22] Filed: Jul. 11, 1986

[51] Int. Cl.[4] .............................................. A61M 5/00
[52] U.S. Cl. ...................................... 604/175; 604/93
[58] Field of Search ............... 623/8; 128/1 R; 604/8, 604/9, 10, 86, 88, 93, 891, 175

[56] References Cited

U.S. PATENT DOCUMENTS

| 3,310,051 | 3/1967 | Schulte | 604/175 |
| 3,640,269 | 2/1972 | Delgado | 128/760 |
| 3,783,868 | 1/1974 | Bokros | 604/891.1 |
| 3,971,376 | 7/1976 | Wichterle | 424/423 |
| 4,108,173 | 8/1978 | Slivenko et al. | 604/175 |
| 4,190,040 | 2/1980 | Schulte | 623/8 |
| 4,464,178 | 8/1984 | Dalton | 604/174 |
| 4,490,137 | 12/1984 | Moukheibir | 604/175 |
| 4,543,088 | 9/1985 | Bootman et al. | 604/175 |
| 4,634,443 | 1/1987 | Haber | 128/1 R |
| 4,673,394 | 6/1987 | Fenton, Jr. et al. | 604/175 |
| 4,705,501 | 11/1987 | Wigness et al. | 604/175 X |
| 4,710,167 | 12/1987 | Lazorthes | 604/891 |
| 4,710,174 | 12/1987 | Moden et al. | 604/175 |

Primary Examiner—Dalton L. Truluck
Assistant Examiner—Frank Wilkins
Attorney, Agent, or Firm—Richard L. Hansen

[57] ABSTRACT

An implantable drug delivery depot has penetrable inlet means which define a first plane and anchor means which define a second plane. According to the invention, the first and second planes are substantially perpendicular. When the depot is implanted with the anchor means parallel to the skin surface, the inlet means is oriented so that a hypodermic needle penetrating the inlet means is nearly parallel to the skin surface, reducing the danger of dislodgement of the needle from the inlet.

4 Claims, 1 Drawing Sheet

IMPLANTABLE FLUID DISPENSER

This invention relates to means and methods for the selective targeting of liquid medications and the controlled release of therapeutic fluids in the body, especially to means which are surgically implanted in the body.

The currently accepted method for delivery of therapeutic fluids to the body is through the use of a hypodermic needle attached to a suitable skin anchoring mechanism, e.g., a butterfly needle set, whereby the needle is advanced parallel to the skin into a suitable vein or artery for delivery of the drug to the blood stream or to an internal body cavity for selective regional therapy. This method of drug delivery is quite adequate for numerous liquids and for general venous blood stream delivery. In the delivery of severely harsh or potent drugs, specifically cytotoxic drugs used in cancer chemotherapy, numerous problems with the usual IV drug delivery practices arise.

Extravisation of the drug with severe tissue damage, deterioration of the vessel from the normally toxic drug, dilution of the drug upon delivery, and short lifetime of the drug in the bloodstream, etc. are a few of the negative aspects of standard intravenous drug deliver when cytotoxic drugs used in cancer therapy are delivered by the accepted method. In conventional intravenous drug administration into a vein with a standard butterfly needle infusion set, extravisation of the drug, i.e., the accidental, unintended delivery of the drug outside the vein, can occur by either missing the veing entirely or by advancing the needle too far into the vessel and passing completely through the vein.

It is known in the art of drug therapy to implant a fluid receptacle beneath the skin, i.e., a penetrable hollow capsule or container. The receptacle is filled from time to time by hypodermic injection with a multidose quantity of a drug. The drug is delivered slowly and continuously, e.g., via an outlet catheter or drug permeable membrane, to a site in the body requiring medication. With this technique the drug is delivered to the site relatively undiluted by body fluids, and the drug is more effective than when injected intramuscularly or into the blood stream. This technique is especially useful with certain cytotoxic drugs used in cancer chemotherapy and also has the advantage of decreasing the number of times the skin must be punctured, thereby reducing the risk of trauma and infection.

The apparatus may also be used to obtain samples of fluid from selected sites in the body. In this mode, the fluid is collected in the subcutaneous reservoir and periodically withdrawn from the reservoir by hypodermic syringe.

A number of such receptacles have been disclosed. For example, U.S. Pat. No. 3,971,376 describes a needle-penetrable capsule backed with an impenetrable wall extended to provide a suture anchor for securing the receptacle to subcutaneous tissue. U.S. Pat. No. 3,783,868 discloses a receptacle having a flat-surfaced, penetrable elastomeric plug or septum inlet; a stabilizing flange extension, which parallels the skin, is provided to secure the receptacle in the body. U.S. Pat. No. 4,464,178 describes another implantable fluid receptacle having flattened, penetrable septum inlet means and a base suturable to fascia which underlie the skin. U.S. Pat. Nos. 3,310,051 and 3,640,269 disclose other implantable receptacles. In each of these receptacles the inlet means and means for secruing the reservoir in the body are oriented such that the reservoir is penetrated by a needle or other conduit directed substantially perpendicular to both the skin and the plane of the reservoir inlet means. For many applications this orientation of the conduit to the skin presents no difficulties.

However, in some situations it is desirable to maintain transcutaneous connection to the reservoir for an extended period of time, hours or days. In these situations it is very difficult to keep a needle or other conduit which is oriented perpendicular and anchored to the surface of the skin from becoming dislodged from the reservoir inlet means, especially if the patient is physically active. Muscular contractions tend to swell the skin in the area of conduit penetration, forcing the conduit from the septum or other inlet means. The present invention is directed primarily to solving this problem. Other objectives will become apparent hereinafter.

Consequently, this invention provides a drug delivery depot for implantation which comprises a rigid walled reservoir including at least one drug outlet and penetrable inlet means, with the inlet means defining a first plane, in combination with reservoir anchor means defining a second plane, said first and second planes being substantially perpendicular. This construction provides inlet means which lie in a plane substantially perpendicular to the surface of the skin when the anchor means is secured, e.g., sutured to the fascia, beneath the skin. Penetration of the inlet with a transcutaneous conduit, in the design-intended fashion, normal to the first plane, places the conduit substantially parallel to the skin; the conduit is readily secured to the skin as an ordinary IV conduit would be secured and is thereby rendered resistant to dislodgement.

This invention will be more readily understood by reference to the drawings which accompany this specification and the detailed description which follows.

Figure 1:
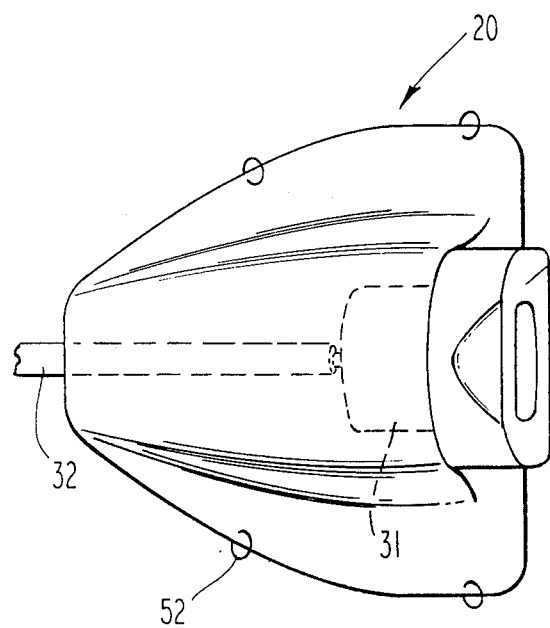
FIG. 1 is a top plan view of one embodiment of the implantable fluid dispenser of this invention, sutures 52 not being a part of the invention, but illustrative only.
Figure 2:
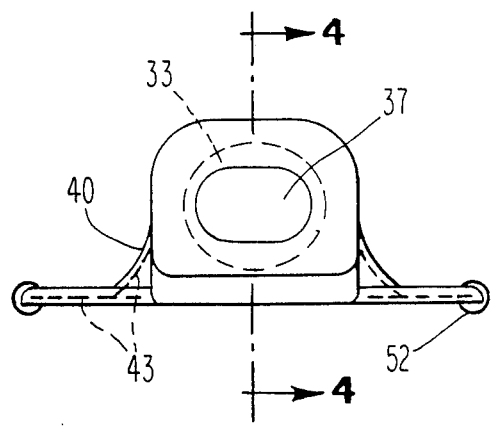
FIG. 2 is an end view of the dispenser shown in FIG. 1
Figure 3:
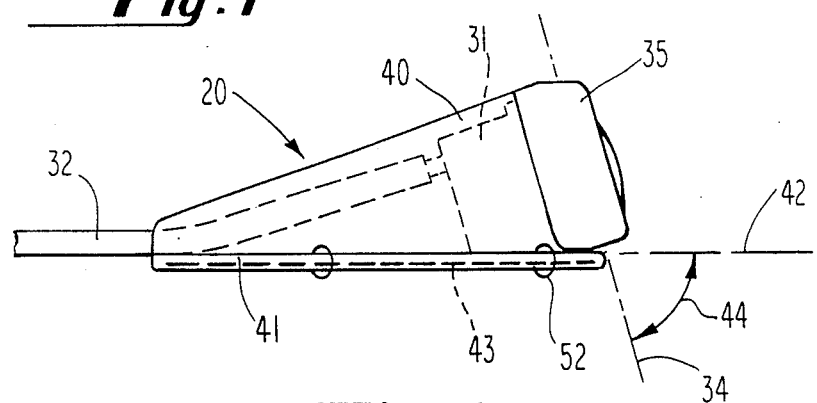
FIG. 3 is a side view of the dispenser shown in FIG. 1.
Figure 4:
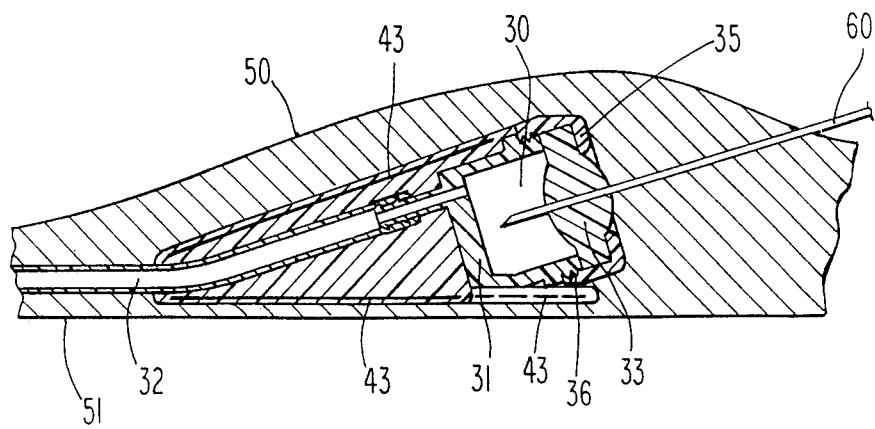
FIG. 4 is a cross-sectional view taken along line 4—4 of FIG. 2 showing the dispenser in the intended implanted state.

With reference to the drawings, drug depot 20 includes reservoir body 31 which encloses drug reservoir 30. Reservoir 30 is provided with drug outlet 32, which is led to the site requiring medication. Penetrable inlet septum 33 seals the reservoir, being compressed against body 31 by means of mating threads 36 on body 31 and retaining ring 35. Alternatively, retaining ring 35 may be joined to body 31 via a suitable adhesive or other fixation means. The flattened septum defines a first plane 34.

Inlet septum 33 preferably presents an oval or eliptical aspect in plane 34, with the long axis of the oval parallel to the surface of the skin. This can be effected with a circular septum by providing an oval window 37 in retaining ring 35. In a subcutaneously implanted drug delivery depot, placed under the skin in the fascia, the size of the septum is limited by the ability of the body to accept or accommodate a bulky device. As the total area of the septum increases in plane 34, the overall size of the depot must increase because the septum is held under compression by retaining ring 35. To maintain the required compression, the size of the depot must increase as the septum area is increased. A septum with a large, unobstructed window in plane 34 is desirable due to the difficulty of accessing the septum under the skin. Yet the larger the depot, the more pressure put on the skin and the greater the possibility of erosion of the depot through the skin.

The design parameters of minimal depot size and large septum area are diffuclt constraints to minimize and maximize, respectively. The oval or eliptical septum configuration accomplishes that optimization. By making the septum oval or eliptical, the puncturable area is increased in a manner that does not create a thicker, higher profile device.

Reservoir boduy 31 and retaining ring 35 are conveniently produced from medically acceptable plastics or metals; for example, polysulfone plastic or stainless steel. The rigid reservoir body prevents extravisation of the drug by containing and holding the access needle, preventing dislocation or advancement of the needle beyond the reservoir, while permitting the entry of the needle to be parallel to the skin as in conventional IV administration.

In order that inlet septum 33 will be readily penetrated to introduce fluid into reservoir 30, yet reseal itself when fluid conduit 60 is withdrawn, the septum may be constructed of a medically acceptable rubber, such as silicone rubber, suitable types of which are well known in the art.

Reservoir body 31 may be potted in a medically acceptable resin, such as silicone, to present fairing 40. Whether or not ffairing 40 is present, a substantially flat suture flange 41 is affixed to the drug depot, defining a second plane 42. Flange 41 may contain embedded fabric 43 and is intended to hold sutures 52 anchoring the drug depot beneath skin 50 to underlying fascia 51.

It will be evident that the drug depot can take various shapes and forms, since these are not critical elements, but the relationship between the inlet means and the anchor means is an important feature in order to obtain the advantages this invention confers on an implanted drug reservoir. That is, it is required that a first plane, defined, e.g., by the septum or other inlet means and normal to the intended direction of needle insertion, and a second plane, defined, e.g., by the suture flange and parallel to the skin, be substantially perpendicular. That is, angle 44 should be about 65-100 degrees, preferably about 75 degrees. When angle 44 is within these limits, conduit 60 enters the depot substantially parallel to the skin, is readily anchored to the skin, and resists spontaneous dislodgement.

What is claimed is:

1. An implantable drug delivery depot for transcutaneous access by a conduit directed substantially parallel to the skin which comprises
   a rigid-walled drug reservoir,
   a flattened, penetrable drug reservoir inlet septum which defines a first plane,
   a substantially flat reservoir anchoring flange which defines a second plane, said first and second planes being substantially perpendicular, together with
   a tubular drug reservoir outlet adapted to avoid inadvertent penetration by the conduit, said outlet being bent or directed at an angle away from said flange to enter said reservoir remote from the conduit tip.

2. The depot of claim 1 wherein said inlet presents an oval or eliptical aspect in said first plane.

3. The depot of claim 1 wherein said flange is an elastomeric material containing embedded fabric.

4. The depot of claim 1 wherein the angle between said first and second planes is about 65-100 degrees.

* * * * *